(12) United States Patent
Gittings et al.

(10) Patent No.: US 7,137,962 B2
(45) Date of Patent: Nov. 21, 2006

(54) DEVICES AND METHODS FOR USE IN PERFORMING TRANSMYOCARDIAL CORONARY BYPASS

(75) Inventors: Darin C. Gittings, Sunnyvale, CA (US); A. Adam Sharkawy, Redwood City, CA (US); Alan R. Rapacki, Redwood City, CA (US); Gilbert S. Laroya, Santa Clara, CA (US)

(73) Assignee: Medtronic, Inc., Minneapolis, MN (US)

( * ) Notice: Subject to any disclaimer, the term of this patent is extended or adjusted under 35 U.S.C. 154(b) by 534 days.

(21) Appl. No.: 10/011,630

(22) Filed: Oct. 22, 2001

(65) Prior Publication Data

US 2003/0158573 A1 Aug. 21, 2003

Related U.S. Application Data

(63) Continuation-in-part of application No. 09/023,492, filed on Feb. 13, 1998, now abandoned.

(51) Int. Cl.
*A61N 5/00* (2006.01)
*A61F 2/04* (2006.01)

(52) U.S. Cl. .............................. 604/8; 600/16; 623/23.7
(58) Field of Classification Search ................ 128/898; 604/8, 9, 10; 600/16; 623/23.7
See application file for complete search history.

(56) References Cited

U.S. PATENT DOCUMENTS

| | | | |
|---|---|---|---|
| 5,429,144 A * | 7/1995 | Wilk | 128/898 |
| 6,250,305 B1 * | 6/2001 | Tweden | 128/898 |
| 6,517,558 B1 | 2/2003 | Gittings et al. | |
| 6,651,670 B1 | 11/2003 | Rapacki et al. | |
| 6,652,540 B1 | 11/2003 | Cole et al. | |
| 6,808,498 B1 | 10/2004 | Laroya et al. | |
| 2001/0004699 A1 | 6/2001 | Gittings et al. | |
| 2001/0025643 A1 | 10/2001 | Foley | |
| 2001/0041902 A1 | 11/2001 | Lepulu et al. | |
| 2002/0004663 A1 | 1/2002 | Gittings et al. | |
| 2002/0077566 A1 | 6/2002 | Laroya et al. | |
| 2002/0144696 A1 | 10/2002 | Sharkawy et al. | |
| 2002/0161424 A1 | 10/2002 | Rapacki et al. | |
| 2004/0077987 A1 | 4/2004 | Rapacki et al. | |
| 2004/0167444 A1 | 8/2004 | Laroya et al. | |
| 2004/0168691 A1 | 9/2004 | Sharkawy et al. | |
| 2005/0043781 A1 | 2/2005 | Foley | |

FOREIGN PATENT DOCUMENTS

| | | |
|---|---|---|
| EP | 0 121 795 A2 | 10/1984 |
| WO | WO9940868 A1 | 8/1999 |
| WO | WO0021461 A2 | 4/2000 |
| WO | WO0041633 A1 | 7/2000 |
| WO | WO0021461 C2 | 9/2000 |
| WO | WO0117440 A1 | 3/2001 |
| WO | WO0041633 C2 | 7/2001 |

* cited by examiner

*Primary Examiner*—Corrine McDermott
*Assistant Examiner*—Thomas Sweet
(74) *Attorney, Agent, or Firm*—Michael Jaro; Jeffrey J. Hohenshell

(57) ABSTRACT

Devices and methods utilized in performing transmyocardial coronary bypass include retractors used to engage and support myocardial tissue, and mechanisms for supporting coronary vessels so as to allow precise entry into a vessel lumen. In addition, various conduits are provided having a configuration that permits their positioning in a heart wall to place a coronary vessel in communication with a heart chamber.

1 Claim, 14 Drawing Sheets

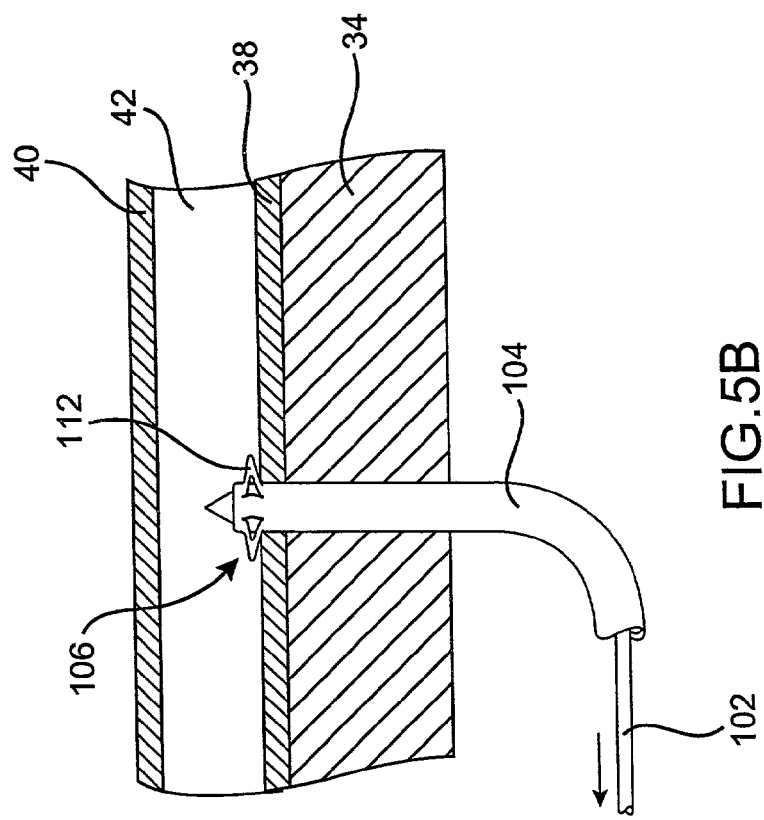
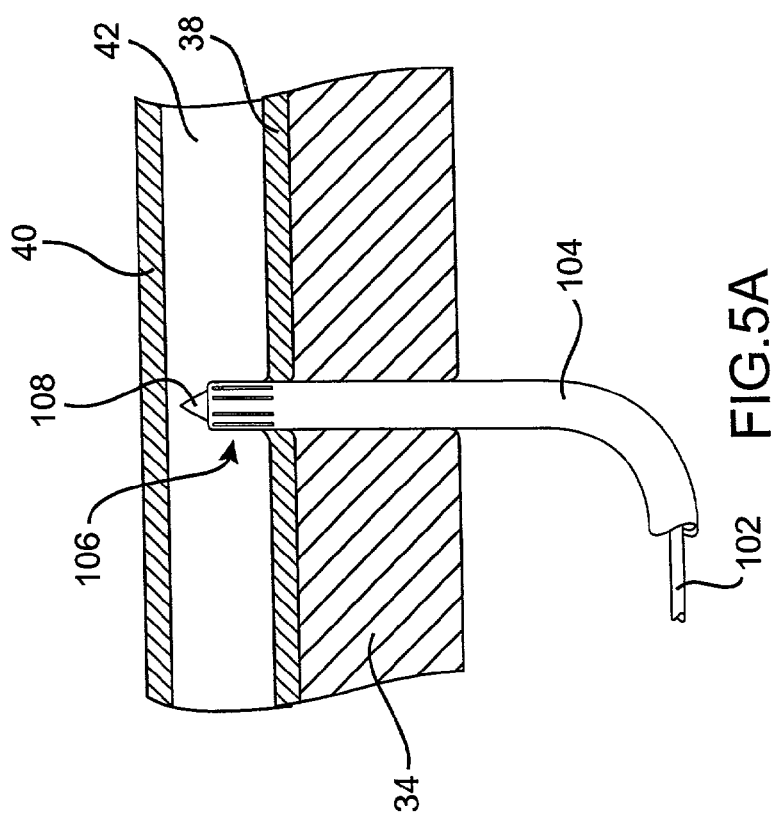

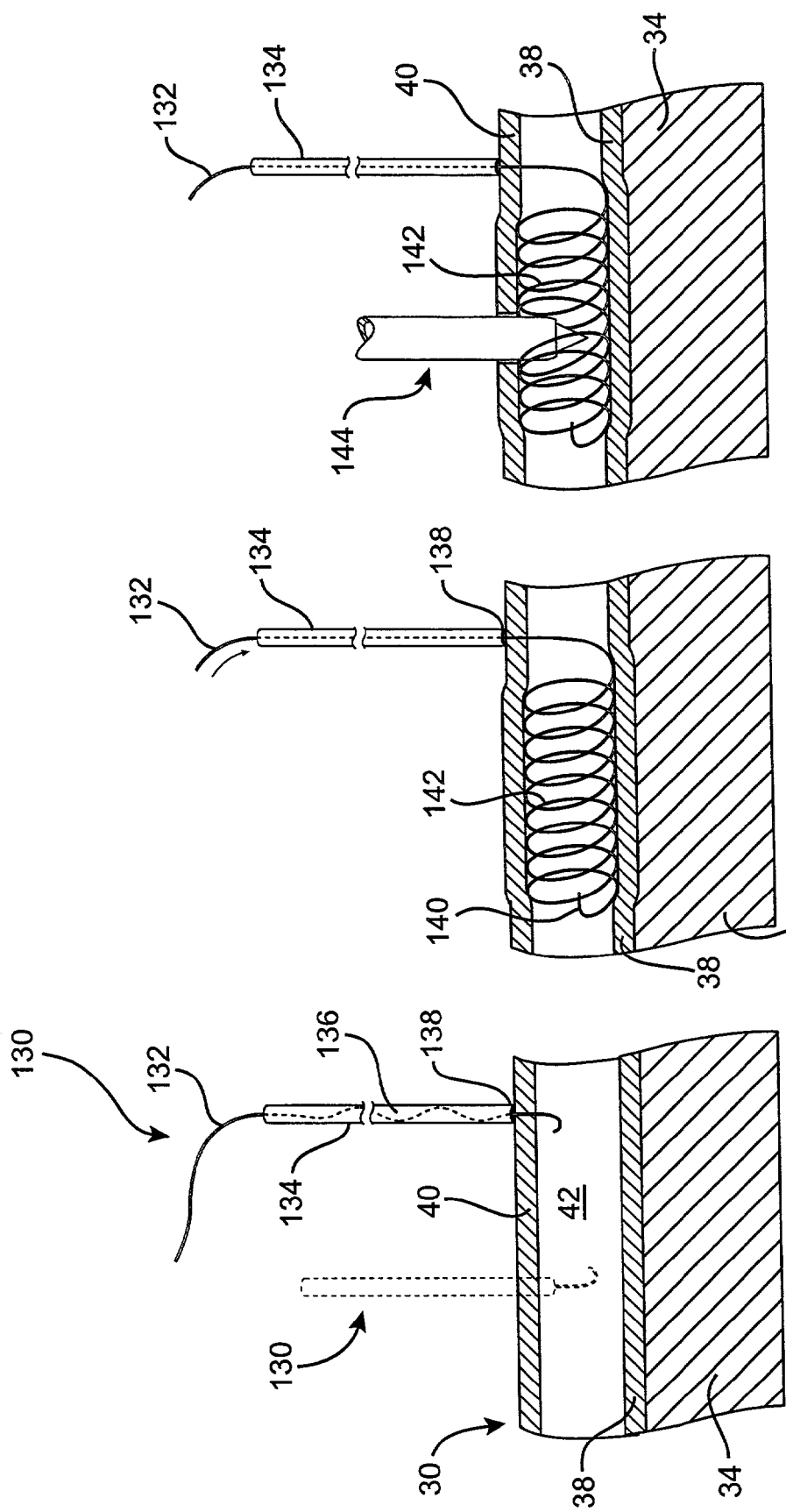

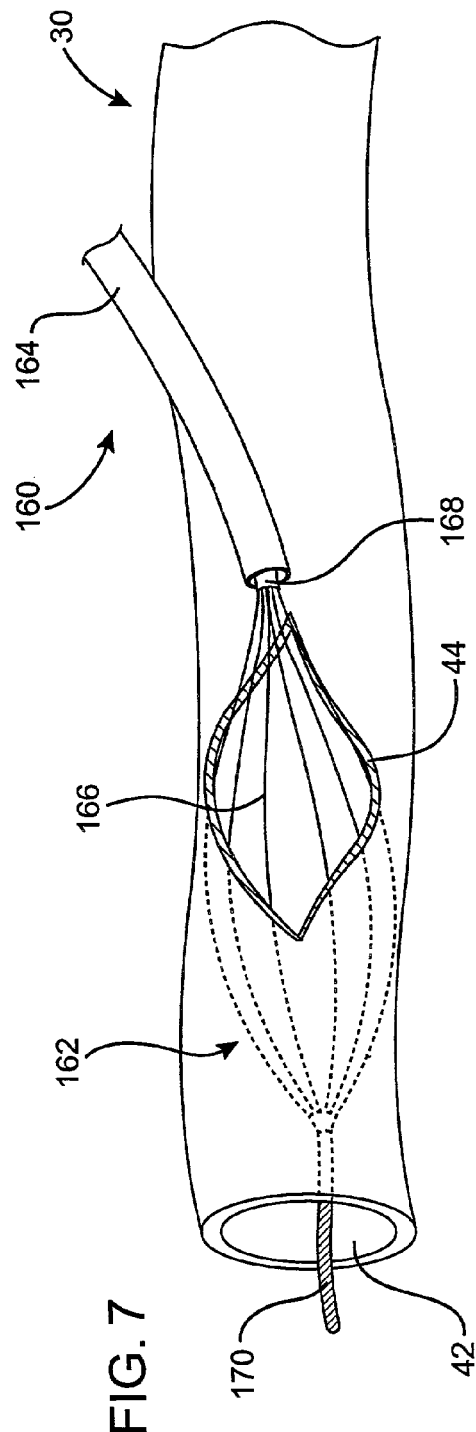
FIG. 7
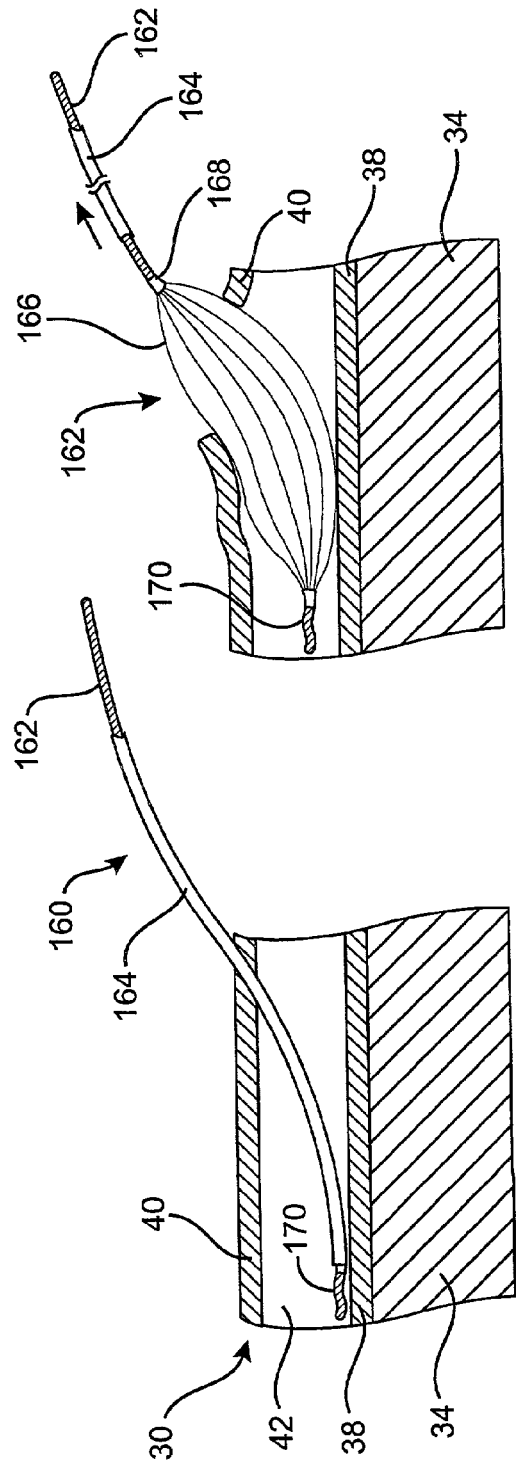
FIG. 8A
FIG. 8B

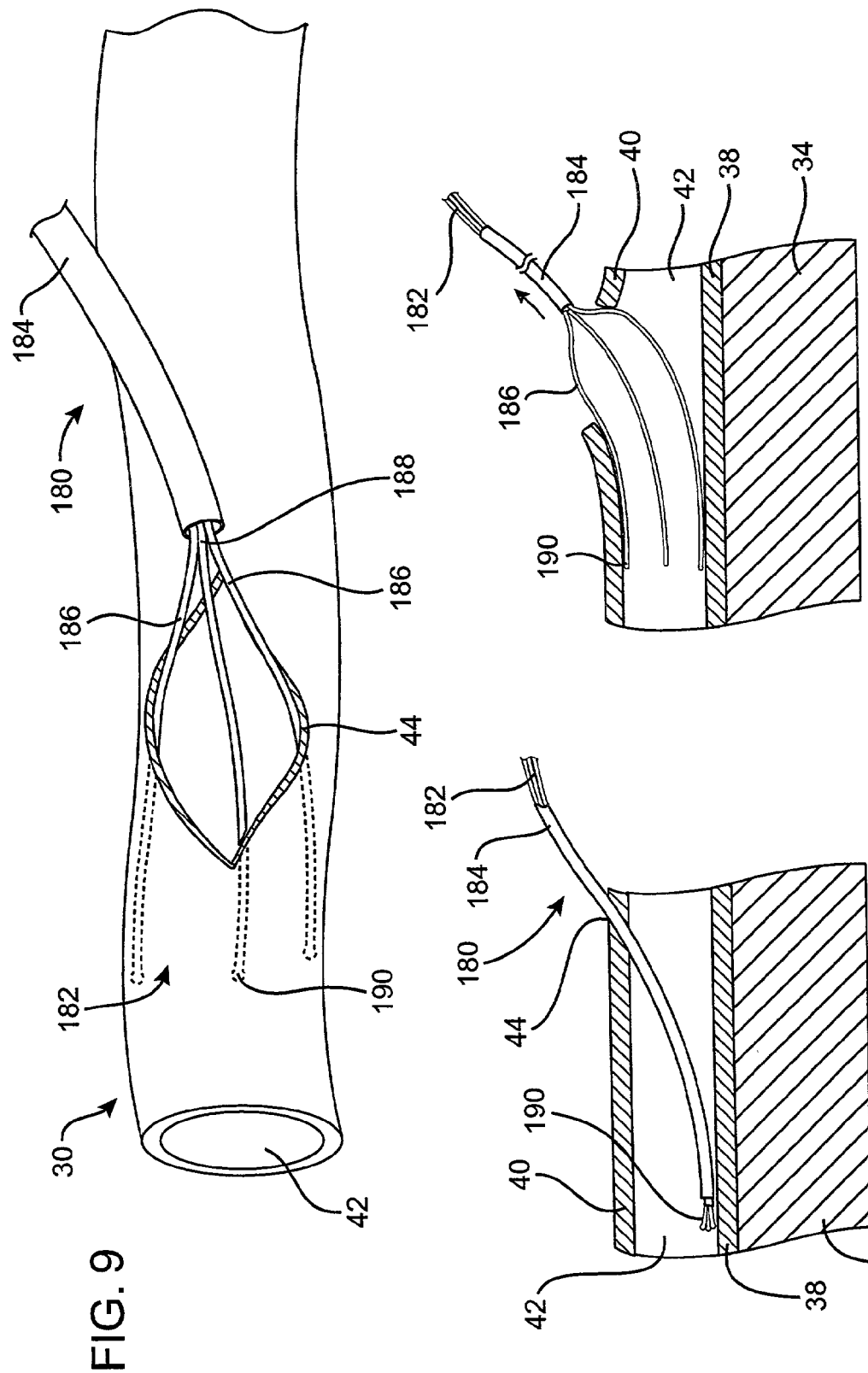

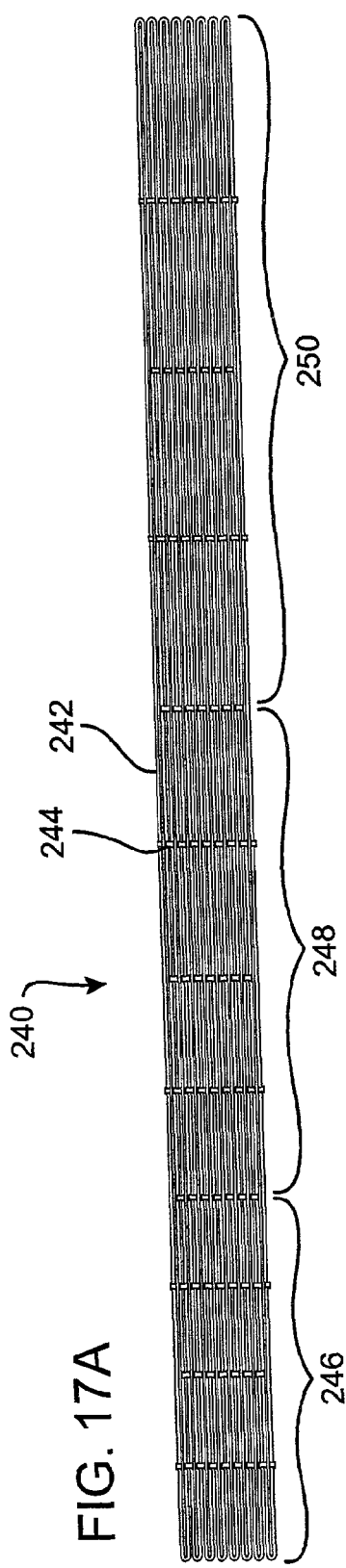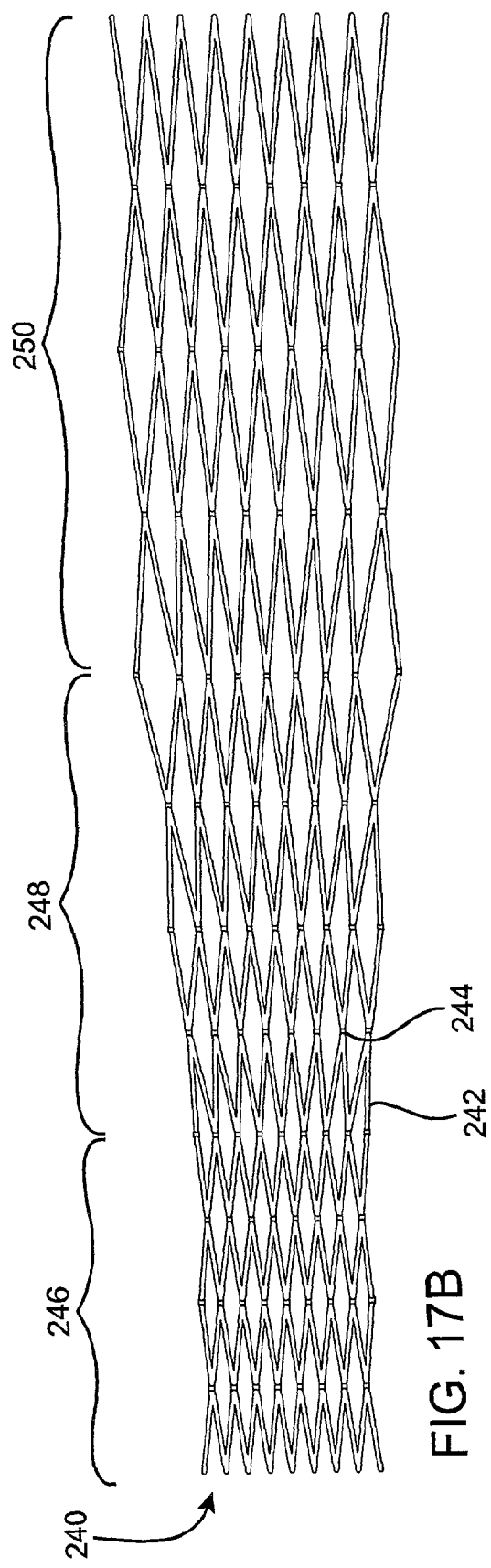
FIG. 17A
FIG. 17B

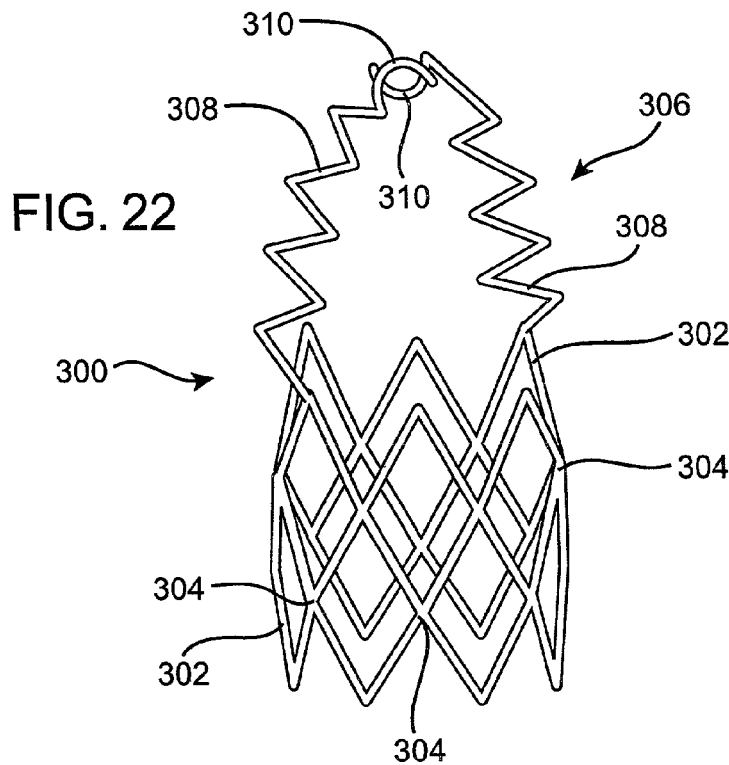
FIG. 22
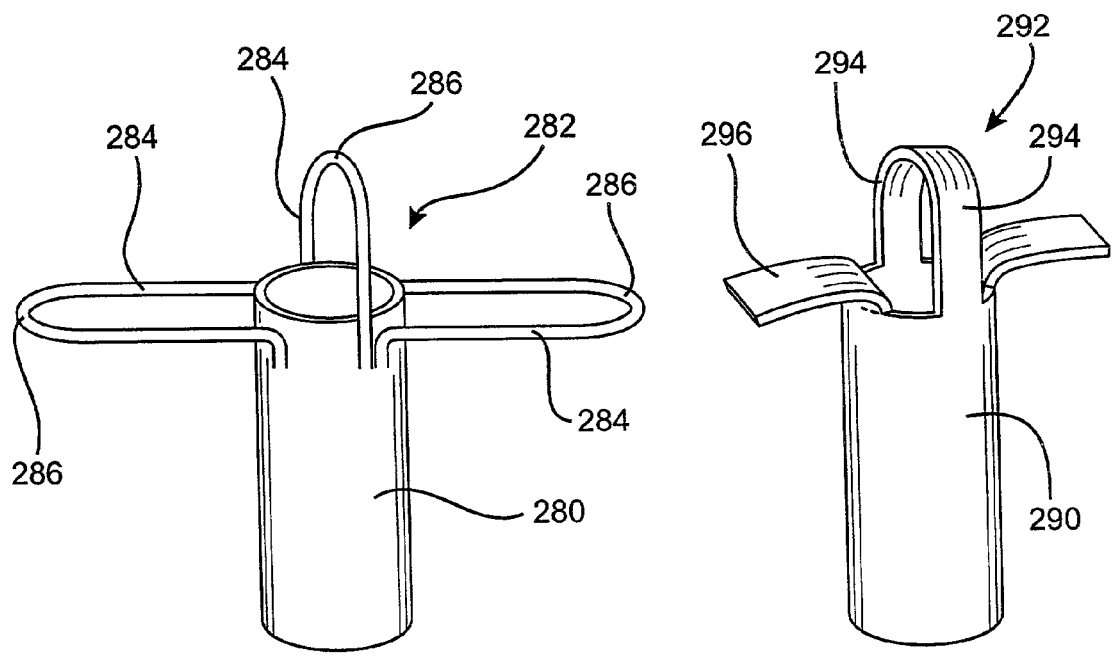
FIG. 20
FIG. 21

DEVICES AND METHODS FOR USE IN PERFORMING TRANSMYOCARDIAL CORONARY BYPASS

CROSS-REFERENCE TO RELATED APPLICATIONS

This application is a continuation-in-part of application Ser. No. 09/023,492, filed Feb. 13, 1998 now abandoned, and entitled "Methods and Devices Providing Transmyocardial Blood Flow to the Arterial Vascular System of the Heart," the entire subject matter of which application is incorporated herein by reference.

BACKGROUND OF THE INVENTION

1. Field of the Invention

The invention relates to treating heart disease, and more particularly systems, devices and methods for reestablishing or improving blood flow to the myocardium.

2. Description of Related Art

Despite the considerable advances that have been realized in cardiology and cardiovascular surgery, heart disease remains the leading cause of death throughout much of the world. Coronary artery disease, or arteriosclerosis, is the single leading cause of death in the United States today. As a result, those in the cardiovascular field continue the search for new and improved treatments.

Coronary artery disease is currently treated by interventional procedures such as percutaneous transluminal coronary angioplasty (PTCA), atherectomy and intracoronary stenting, as well as surgical procedures including coronary artery bypass grafting (CABG). The goal of these procedures is to reestablish or improve blood flow through occluded (or partially occluded) coronary arteries, which is accomplished, for example, by enlarging the blood flow lumen of the artery or by forming a bypass that allows blood to circumvent the occlusion. What procedure(s) is used typically depends on the severity and location of the blockages. When successful, these procedures restore blood flow to myocardial tissue that had not been sufficiently perfused due to the occlusion.

Technological and procedural advances have improved the results obtained by the medical procedures now used to treat heart disease, and in particular coronary artery disease. There is, however, still much room for improvement. For that reason there remains a need in the art for new and improved systems, devices and methods for treating heart disease such as arteriosclerosis.

SUMMARY OF THE INVENTION

In one embodiment, the invention provides a device and method for engaging tissue of a coronary vessel or heart wall during a cardiovascular procedure. A device constructed according to this embodiment includes first and second members coupled together so as to permit relative movement. A tissue engaging mechanism is coupled to the first and second members and moves between first and second positions. In the preferred embodiment, the first and second positions are collapsed and expanded orientations. The tissue engaging mechanism includes at least one tissue engaging member that contacts engage body tissue when in the expanded orientation.

A method carried out according to this embodiment includes steps of providing a tissue support device having a tissue engaging mechanism configured to assume an expanded, tissue supporting orientation, positioning the tissue support device through the wall of a patient's heart and locating the tissue engaging mechanism adjacent tissue, and placing the tissue engaging mechanism in the expanded, tissue supporting orientation in engagement with the tissue.

In another embodiment, the invention provides a device and method for supporting a wall of a vascular structure in order to access the lumen of the vascular structure. A device constructed according to this embodiment includes a support structure adapted to be positioned in the lumen of a vascular structure, the support structure comprising a plurality of support elements coupled together so as to be movable relative to each other. The support elements move relative to each other to move the support structure from a collapsed orientation to an expanded orientation in order to support a wall of a vascular structure, and are sized and configured so that when the support structure is in the expanded orientation the support elements engage the wall of the vascular structure to prevent the wall from collapsing.

Another device constructed according to this embodiment includes an introducer having a hollow interior and an elongated support member configured to be generally coiled when in an unbiased orientation and generally straight when in a biased orientation. The interior of the introducer is sized and configured to receive the elongated support member and hold the support member in the generally straight, biased orientation. The elongated support member is moved from the straight, biased orientation within the interior of the introducer to the coiled, unbiased orientation upon entering the interior of the vascular structure to support the vascular structure.

A method carried out according to this embodiment includes steps of positioning a support within an interior of a vascular structure such that the support contacts and supports a wall of the vascular structure, and introducing a medical device into the interior of the vascular structure by passing the device through the wall of the vascular structure and through the support.

In another embodiment, the invention provides a device and method for stabilizing an area of a patient's heart adjacent a coronary vessel. A device constructed according to this embodiment includes a base configured to be positioned adjacent a coronary vessel of a patient's heart, the base having at least one opening for accessing the coronary vessel. At least one tissue engaging element is coupled to the base so as to be movable with respect to the base, the tissue engaging element having a portion configured to securely engage the wall of a patient's heart in order to stabilize the wall of the heart upon moving the tissue engaging element with respect to the base. An actuator is provided for imparting relative movement to the base and the tissue engaging element in order to stabilize the heart while accessing the coronary vessel through the opening in the base.

In yet another embodiment, the invention provides a conduit for placing a coronary vessel of a patient's heart in communication with a heart chamber. The conduit is in the form of a tubular element including first and second portions having different cross-sectional sizes and a bore defining a blood flow path. The cross-section of the first portion of the tubular element is larger than the cross-section of the second portion such that the tubular element is generally funnel-shaped, and the first and second portions of the tubular element are generally aligned so that the bore defines a generally straight blood flow path.

In still another embodiment, the invention provides a conduit for communicating a chamber of a patient's heart with a coronary vessel. The conduit is in the form of an expandable stent including first and second portions having different cross-sectional sizes when the stent is expanded. Each of the first and second portions of the stent includes strut members disposed along a first direction when the stent is unexpanded and along a second direction when the stent is expanded, the second direction being transverse to the first direction. The strut members of the first portion are longer than the strut members of the second portion so that the stent is generally funnel-shaped when expanded.

In another embodiment, the invention provides a conduit is in the form of an expandable tubular element having first and second portions with different cross-sectional sizes. This tubular element is preferably a coronary stent constructed so that the first and second portions are disposed in an orientation that provides the stent with maximum radial strength when expanded.

In a final embodiment, the invention provides a conduit for placing a coronary vessel in communication with a heart chamber, the conduit including a vessel support mechanism configured to contact and support the vessel wall when the conduit is positioned in the heart wall.

BRIEF DESCRIPTION OF THE DRAWINGS

The invention will be better understood from the following detailed description of preferred embodiments thereof, taken in conjunction with the accompanying drawing figures, wherein:

FIGS. 5A–5B are elevation views, in section, illustrating another preferred construction of a tissue engaging device according to the embodiment of FIGS. 3A–3B, wherein the device is shown being used to engage the heart wall shown in FIGS. 2–2A;

FIGS. 6A–6C are elevation views, in section, sequentially illustrating a vessel support device constructed according to another embodiment of the invention being used to support the wall of a vascular structure;

FIG. 7 is a perspective view of a vessel support device constructed according to an alternative embodiment of the invention, the device being shown positioned in the interior of a vascular structure;

FIGS. 8A–8B are elevation views, in section, sequentially illustrating the device shown in FIG. 7 being used to support a coronary artery of the heart shown in FIGS. 2–2A;

FIG. 9 is a perspective view of a vessel support device constructed according to another alternative embodiment of the invention, the device being shown positioned in the interior of a vascular structure;

FIGS. 10A–10B are elevation views, in section, sequentially illustrating the device shown in FIG. 9 being used to support a coronary artery of the heart shown in FIGS. 2–2A;

FIGS. 17A–17B are elevation views showing a conduit constructed according to still another embodiment of the invention, wherein the conduit has a cross-sectional size that varies over its length;

FIG. 20 is a perspective view of an alternative embodiment of a conduit for placing a coronary vessel in communication with a heart chamber while internally supporting the interior of the vessel;

FIG. 21 is a perspective view of another alternative embodiment of a conduit for placing a coronary vessel in communication with a heart chamber while internally supporting the interior of the vessel; and FIG. 22 is a perspective view of yet another alternative embodiment of a conduit for placing a coronary vessel in communication with a heart chamber while internally supporting the interior of the vessel.

DETAILED DESCRIPTION OF THE PREFERRED EMBODIMENT

Figure 1:
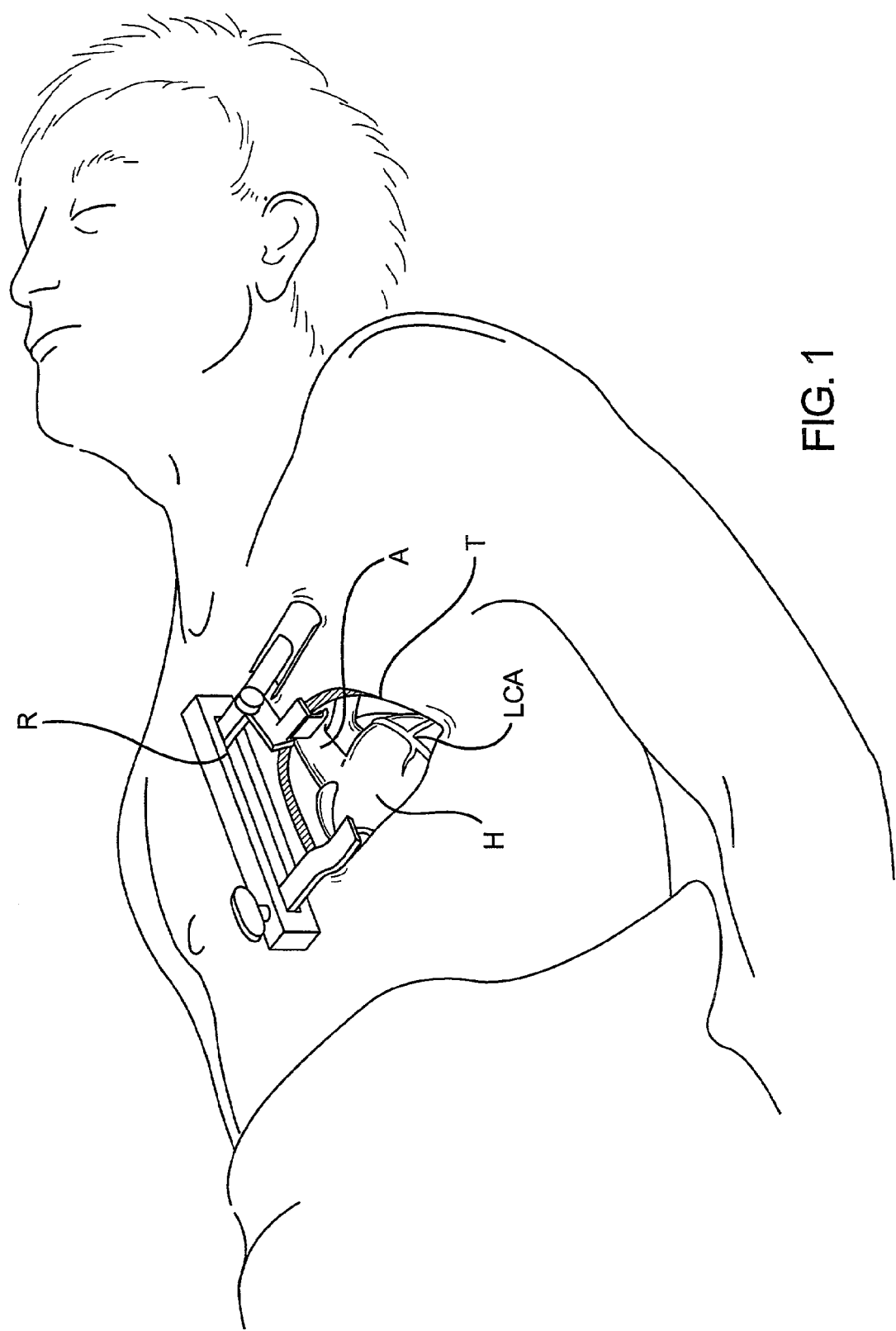
FIG. 1 is a schematic view of a patient prepared to undergo a cardiovascular surgical procedure, the patient's heart being exposed via a retractor positioned in a thoracotomy formed in the patient's chest.

FIG. 1 schematically depicts a patient who has been prepared to undergo a cardiovascular surgical procedure. A thoracotomy T formed in the patient's chest by making an incision between two ribs (not shown) provides access to the thoracic cavity. A retractor, such as the rib retractor R shown in FIG. 1, may be used to spread the ribs and increase access to the heart H and great vessels. The retractor is preferably of a type that in addition to spreading the sides of the incision along a first plane, also raises one side of the incision with respect to the other side to increase the working space around the heart. Any suitable retractor may be used, for example, one of the commercially available rib retractors currently used in minimally invasive cardiac surgery. As shown in FIG. 1, the retractor R provides considerable access to the surfaces of the heart H and great vessels including the aorta A. The left side of the heart as well as the left coronary artery LCA is easily accessible via the thoracotomy T (FIG. 1).

Figure 2:
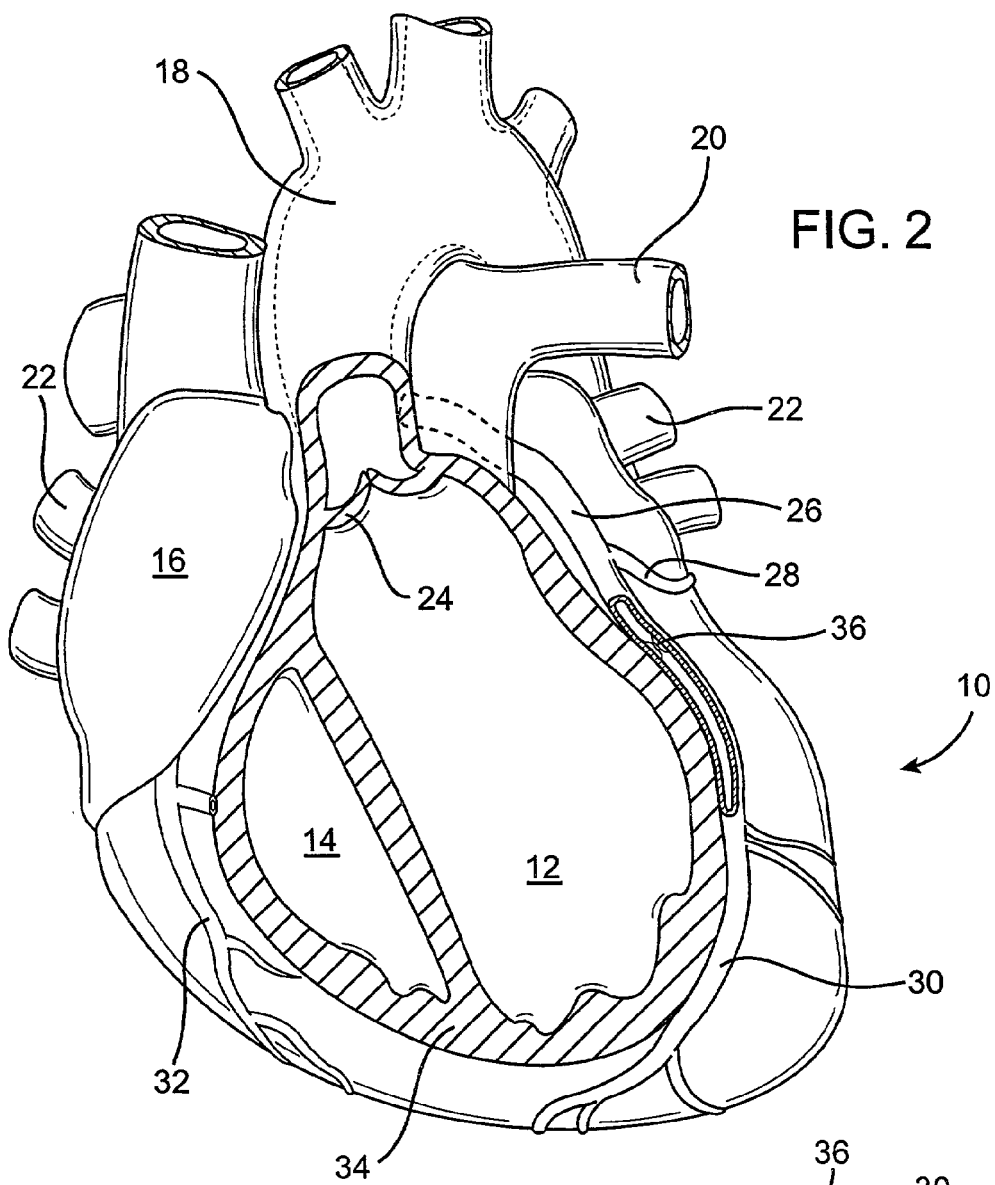
FIG. 2 is a perspective view of the heart shown in FIG. 1, wherein a portion of the heart wall is broken away for clarity.

FIG. 2 is an anterior view of a heart 10 showing the left ventricle 12, right ventricle 14, right atrium 16, aorta 18, pulmonary trunk 20 and pulmonary veins 22. In FIG. 2 the heart 10 is in diastole, or the relaxed phase of the heart cycle, so the aortic valve 24 is shown closed. The left coronary artery 26, including the circumflex branch 28 and the left anterior descending branch (LAD) 30, is visible in this view, as is the right coronary artery 32. The coronary arteries 26, 28, 30, 32 run along the heart wall 34 and deliver oxygenated blood to the tissue comprising the heart wall (epicardium, myocardium and endocardium) while the coronary veins run alongside the arteries and return blood to the coronary sinus (not shown).

Figure 2A:
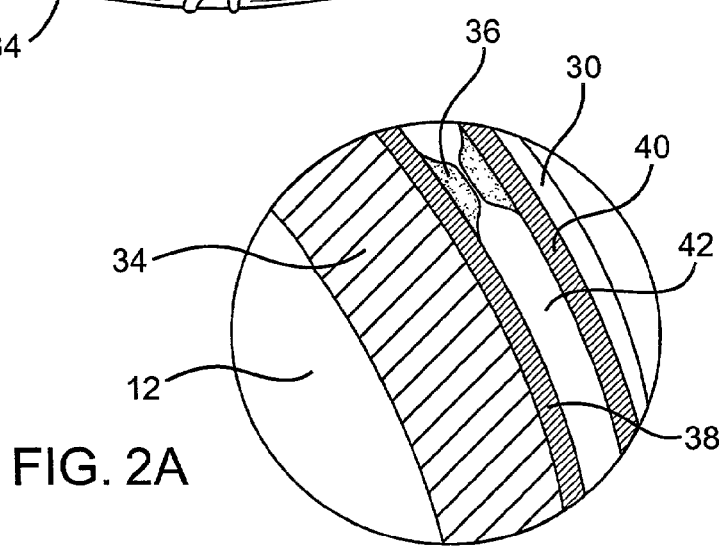
FIG. 2A is an enlarged view of a portion of FIG. 2.

A blockage or occlusion 36 is shown in the LAD 30 and results in partial or complete obstruction of the artery lumen 42, a condition often referred to as narrowing of the arteries. This results in inadequate or no blood flow to the heart wall tissue fed by the portion of the LAD 30 that is downstream of the occlusion 36. FIGS. 2–2A show a portion of the heart wall 34 disposed between the left ventricle 12 and the LAD 30, as well as the inner and outer walls 38, 40 of the LAD 30. The devices and methods of the different embodiments of the invention are illustrated and described in connection with their use on the portion of the heart 10 shown in FIG. 2A. It will be understood, however, that such description is for explanatory purposes and exemplifies only one application for the invention.

Figure 3A:
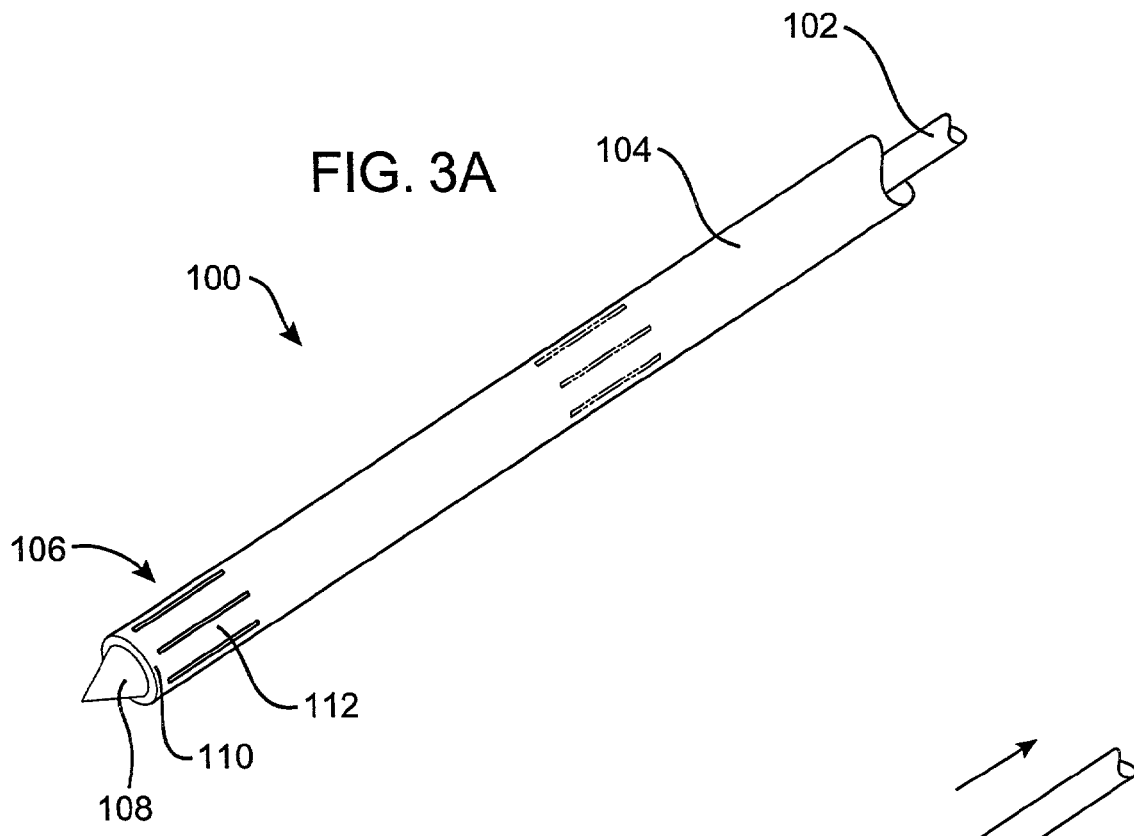
FIGS. 3A–3B are perspective views showing a tissue engaging device constructed according to one embodiment of the invention, the device being shown in collapsed and expanded orientations, respectively.
Figure 3B:
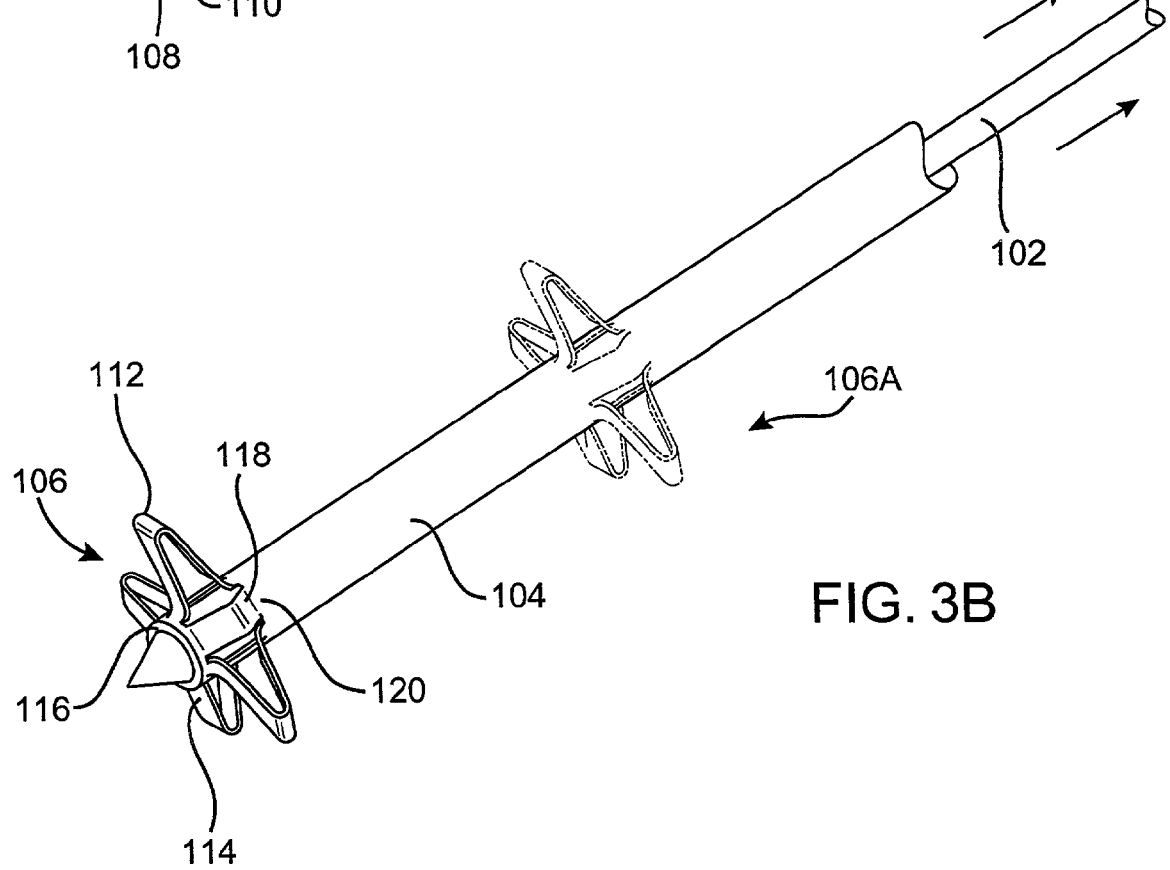

FIGS. 3A–3B illustrate a first embodiment of the invention that provides a device and method for engaging tissue of a coronary vessel or heart wall during a cardiovascular procedure. A preferred device is indicated generally by the reference numeral 100 and includes first and second relatively movable members and a tissue engaging mechanism coupled to the members. In the illustrated embodiment the members comprise first and second coaxial shafts 102, 104 coupled to a tissue engaging mechanism 106. Specifically, the tissue engaging mechanism 106 is coupled to the shafts 102, 104 so that relative movement imparted to the shafts results in the mechanism 106 moving between a collapsed orientation (FIG. 3A) and an expanded, tissue engaging orientation (FIG. 3B).

The first shaft 102 has a distal end 108 which is secured to a distal end 110 of the shaft 104. The tissue engaging mechanism 106 is disposed adjacent the distal ends 108, 110 of the shafts 102, 104 and comprises one or more tissue engaging members 112 which move radially outward when the mechanism is in the expanded orientation. Each tissue engaging member 112 has one end 114 fixed to the distal end 108 of shaft 102 at 116, and another end 118 fixed to the shaft 104 at 120. FIG. 3A shows the tissue engaging mechanism 106 in its collapsed orientation with the members 112 generally straight. FIG. 3B shows the tissue engaging mechanism 106 in its expanded orientation in which the members 112 extend outward in a radial direction. The components of the device 100 may be formed of any suitable material.

The orientation of the tissue engaging mechanism 106 is controlled by imparting relative movement to the shafts 102, 104. The device 100 is preferably introduced into a coronary vessel or heart wall with the tissue engaging mechanism 106 in the low profile orientation shown in FIG. 3A. The device 100 may have a sharpened tip as shown, or it may have a dilating portion that dilates a previously-formed incision. Once passed through the tissue to a desired position, the tissue engaging mechanism 106 is moved to the expanded orientation shown in FIG. 3B in order to engage tissue. This may be achieved by moving the inner shaft 102 in the direction of the arrows with respect to the outer shaft 104, which moves the ends 114, 118 of the tissue engaging members 112 toward each other to expand the mechanism 106. In the orientation shown in FIG. 3B, the device 100 may be used to perform any of various functions, for example, to support, retract or stabilize tissue during a cardiovascular procedure.

Figure 4B:
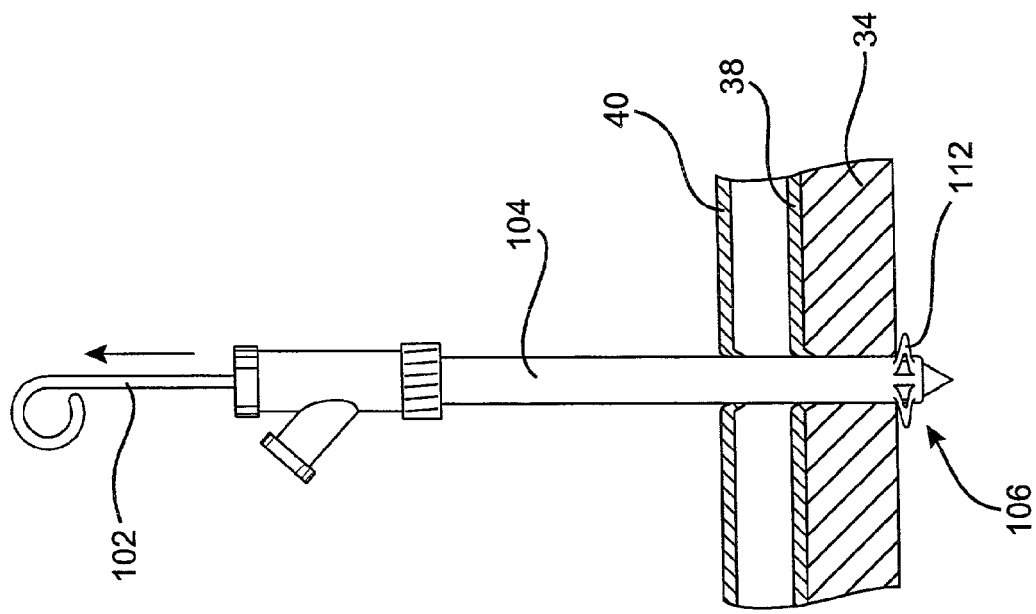
FIGS. 4A–4B are elevation views, in section, illustrating one preferred construction of a tissue engaging device according to the embodiment of FIGS. 3A–3B, wherein the device is shown being used to engage the heart wall shown in FIGS. 2–2A.
Figure 4A:
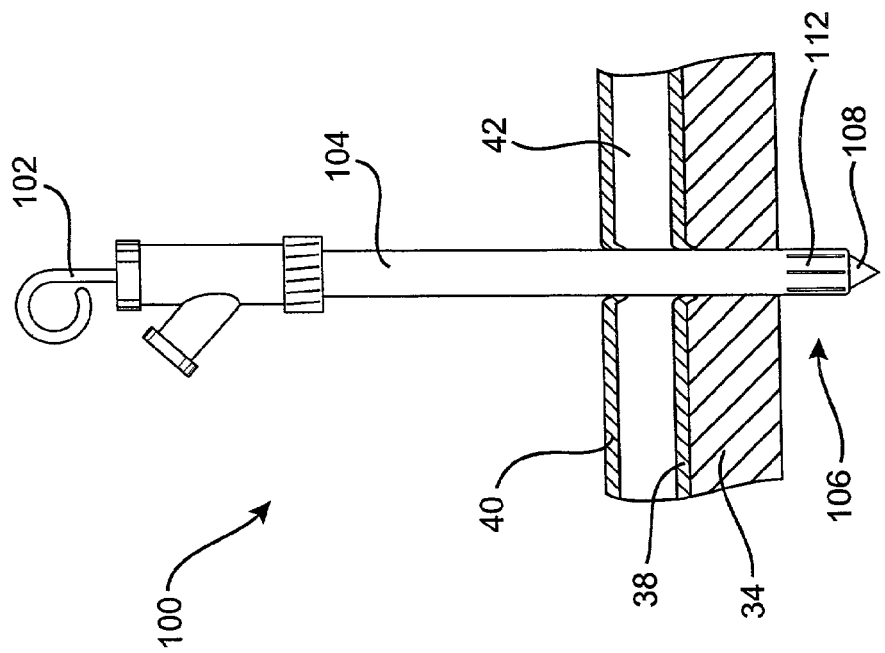

FIGS. 4A–4B show one application of the device 100, namely, to engage the tissue of the wall of a patient's heart. As shown in FIG. 4A, the device 100 is inserted through a coronary vessel such as LAD 30 and the heart wall 34 with the tissue engaging mechanism 106 in its collapsed orientation. Upon moving the tissue engaging mechanism 106 out of the heart wall 34 and into a heart chamber such as left ventricle 12, the shafts 102, 104 are moved with respect to each other to expand the tissue engaging mechanism 106 to the position shown in FIG. 4A. The expanded tissue engaging mechanism 106 may then be used to engage and support the heart wall 34 to facilitate carrying out a cardiovascular procedure, for example, placing a conduit (not shown) in the heart wall to place the coronary vessel in communication with the heart chamber, or forming a channel in the heart wall to place the coronary vessel in communication with the heart chamber.

FIGS. 5A–5B show another application of the device 100, namely, to engage the tissue of the wall of a coronary vessel. As above, the device 100 is introduced with the tissue engaging mechanism 106 in its collapsed orientation, the device being passed through the heart wall 34 and then the inner wall 38 of the LAD 30. Once the tissue engaging mechanism 106 has moved into the lumen 42 of the LAD 30, the shafts 102, 104 are moved with respect to each other to expand the tissue engaging mechanism 106 to the orientation shown in FIG. 5A. The tissue engaging mechanism 106 may then be used to engage and support the wall 38 of the LAD and the heart wall 34 to facilitate carrying out a cardiovascular procedure. Examples of such procedures include placing a conduit (not shown) in the heart wall to place the coronary vessel in communication with the heart chamber, and forming a channel in the heart wall to place the coronary vessel in communication with the heart chamber.

As shown in FIGS. 3A–3B, the device 100 may have a second tissue engaging mechanism 106A so that a body of tissue may be sandwiched between the two mechanisms 106, 106A for added stability.

FIGS. 6A–6C depict another embodiment of the invention that provides a device and method for supporting a wall of a vascular structure in order to access the lumen of the vascular structure. One device constructed according to this embodiment is designated generally by the reference numeral 130 and includes an elongated support member 132 and an introducer 134. The introducer has a bore 136 that is configured to receive the support member 132, as shown in FIG. 6A and preferably has a small diameter in order to minimize the size of the opening in the vascular structure, which in the illustrated embodiment is a coronary vessel and, in particular, LAD 30.

The elongated support member 132 is preferably constructed so as to expand when in an unbiased orientation, i.e., when it is not constrained by the introducer 134. In the preferred embodiment, the support member 132 is constructed to assume a coiled shape when in the unbiased orientation, for example, the helical configuration shown in FIG. 6B. When disposed in the introducer 134, however, the support member 132 is in a biased orientation and assumes a generally straight shape within the bore 136 of the introducer.

An exemplary application for the device 130 will be explained with reference to FIGS. 6A–6C. Initially, as shown in FIG. 6A, an end 138 of the introducer 134 is positioned against the exterior of the wall 40 of the LAD with the elongated support member 132 disposed within the introducer 134. Alternatively, as shown in phantom in FIG. 6A, the end 138 of the introducer 134 may be passed through the wall 40 into the lumen 42 of the LAD 30. If used in this manner, the support member 132 does not need to pierce the tissue of the vascular structure; if used as shown in solid lines in FIG. 6A, an end 140 of the support member 132 is preferably sharpened to pierce through the wall of the vascular structure.

The elongated support member 132 is fed through the introducer 134 into the lumen 42 of the LAD 30. The support member 132 forms a coil 142 as it exits the introducer 134, as shown in FIG. 6B. The support member is constructed so that the coil 142 has a size that contacts and distends slightly the LAD 30, thereby providing support to the LAD to allow precise entry into the lumen 42 of the LAD. A medical device may then be inserted through the wall of the vascular structure and the support member. For example, FIG. 6C shows a medical device 144 inserted through the wall 40 of the LAD 30 and through the coil 142. The device 144 is then removed upon completing the procedure; the elongated support member 132 may then be removed from the LAD 30 by retracting the member back into the bore 136 of the introducer 134.

The elongated support member 132 may be formed of any suitable material having sufficient memory to assume an expanded configuration when unbiased, such as spring wire or nitinol. As an example, the support member 132 could be formed of a length of nitinol wire having an approximate diameter of 0.007 inch that has been wrapped on a suitable mandrel (not shown), such as a stainless steel rod having an approximate diameter of 0.060 inch. The mandrel and wire are then heated to set the shape in the wire which, per se, is known in the art. The mandrel may have two apertures that receive the ends of the nitinol wire and a relief section that causes the end 140 of the support member to roll inward toward the interior of the coil 142, which minimizes the risk of the end 140 damaging tissue.

It will be recognized that the device 130 may be used to support a vascular structure independently of carrying out a medical procedure. As an example, the device 130 could be used to introduce the support member 132 into a coronary artery in order to stent the artery, the coil 142 remaining in place in the same manner as a conventional coronary stent. In this embodiment, it may be desirable to form the other end 146 of the support member 132 so that it too moves toward the interior of the coil 142 upon exiting the introducer 134 to avoid tissue damage.

FIGS. 7 and 8A–8B depict an alternative embodiment of a device and method for supporting a wall of a vascular structure in order to access the lumen of the vascular structure. The device is indicated generally by the reference numeral 160 and is configured to be placed in a collapsed orientation for introduction into a vascular structure and then expanded to contact and support the wall of the structure. The device 160 comprises a support structure 162 removably retained in an introducer 164. The illustrated support structure 162 comprises a plurality of struts 166 that form a basket-like member when moved out of the introducer 164. For example, the struts 166 may be in the form of resilient wires that move away from each other as the support structure 162 exits the introducer 164, the wires extending between proximal and distal portions 168, 170 of the support structure. The introducer 164 may be a sheath or sleeve sized and configured to at least partially surround the support structure 162 and hold the struts 166 together. The respective components may be formed of suitable materials, such as spring wire and a polymer sleeve.

FIG. 7 shows one preferred use of the device 160 wherein the device is inserted through an opening in a vascular structure, such as incision 44 in LAD 30. It will be noted, though, that the device may be passed through a peripheral vessel to a desired location within a vascular structure, and then expanded within the vascular structure by moving the support structure out of the introducer. As shown in FIG. 8A, the device is passed through the incision 44 and into the lumen 42 of the LAD 30. The introducer 164 is then retracted over the proximal portion 168 of the support structure which results in the struts 166 moving away from each other to contact and support the wall of LAD 30. As explained above with respect to the previous embodiment, various medical devices may then be introduced through the wall of the vascular structure and through the support structure 162. Upon completion of the procedure, the introducer 164 is slid back over the struts 166 to collapse the support structure 162, which allows the device 160 to be removed through the incision 44.

FIGS. 9 and 10A–10B illustrate another alternative embodiment of a device and method for supporting a wall of a vascular structure in order to access the lumen of the vascular structure. The device has a construction somewhat similar to the device 160 in FIGS. 7 and 8A–8B. The device is indicated generally by the reference numeral 180 in FIG. 9 and is configured to be placed in a collapsed orientation for introduction into a vascular structure and then expanded to contact and support the wall of the structure. The device 180 comprises a support structure 182 removably retained in an introducer 184. The illustrated support structure 182 includes a plurality of struts 186 which may be in the form of resilient wires that move away from each other as the support structure exits the introducer 184. The struts 186 may be joined at their proximal ends 188 and preferably have distal ends 190 with a non-traumatic configuration to prevent tissue damage. As in the previous embodiment, the introducer 164 may be a sheath or sleeve sized and configured to at least partially surround the support structure 162 to hold the struts 186 together. The materials used in the embodiment of FIG. 7 may be used in this embodiment.

As shown in FIG. 10A, the device 180 is passed through the incision 44 and into the lumen 42 of the LAD 30, and the introducer 184 is then retracted to allow the struts 186 to move away from each other. This results in the support structure 182 assuming the expanded orientation shown in FIG. 10B wherein the struts 186 contact and support the wall of LAD 30. As with the previous embodiments, various medical devices may then be introduced through the wall of the vascular structure and through the support structure 162.

It will be appreciated that the vascular support devices and methods illustrated in the drawings are only preferred embodiments of the invention. This aspect of the invention encompasses supporting the wall of a vascular structure in order to allow precise entry into the lumen, which may be relatively difficult if the wall of the vascular structure is collapsed. Accordingly, many variations of the disclosed devices and methods will be apparent to those skilled in the art. For example, an alternative design utilizes an expandable support that may be in the form of a stent having one or more openings to allow passage of medical devices into the lumen of the vascular structure. The stent could have any desired coverage area with openings provided between adjacent stent elements or formed by removing portions of the stent elements.

Another alternative design comprises a device in the form of a member configured to rest on the exterior of the vascular structure to provide access into the lumen of the structure. The device may have a distal portion shaped somewhat complementarily to the vascular structure to closely engage same. For example, the distal portion could include a concave recess that receives the vascular structure when the device is rested on surrounding tissue. The device preferably has a bore that opens into the recess so that a medical device inserted into the bore passes through the wall of the vascular structure.

Additionally, while the vessel support devices are shown introduced into the vessel through the wall close to or at the area of the vessel that is supported. The support devices could be positioned in an alternative manner, for example, by passing the device through the artery lumen from a location downstream of the area that is supported.

FIGS. 11A–11B and 12A–12B show another embodiment of the invention that provides devices and methods for stabilizing an area of a patient's heart adjacent a coronary vessel. The illustrated device is indicated generally by the reference numeral 200 and comprises a base 202 configured to be positioned adjacent a coronary vessel of a patient's heart. The base 202 has at least one opening 204 which provides access to the coronary vessel, which, in the illustrated embodiment, is the LAD 30. The device 200 also includes at least one, and preferably a plurality, of tissue engaging elements 206 coupled to the base 202 so as to be movable with respect thereto. Each tissue engaging element 206 has an end 208 configured to securely engage the tissue of a patient's heart in order to stabilize the heart, and an end 210 coupled to the base 202. Each end 210 is pivotally attached to the base 202 by a pivot pin 212.

Figure 11A:
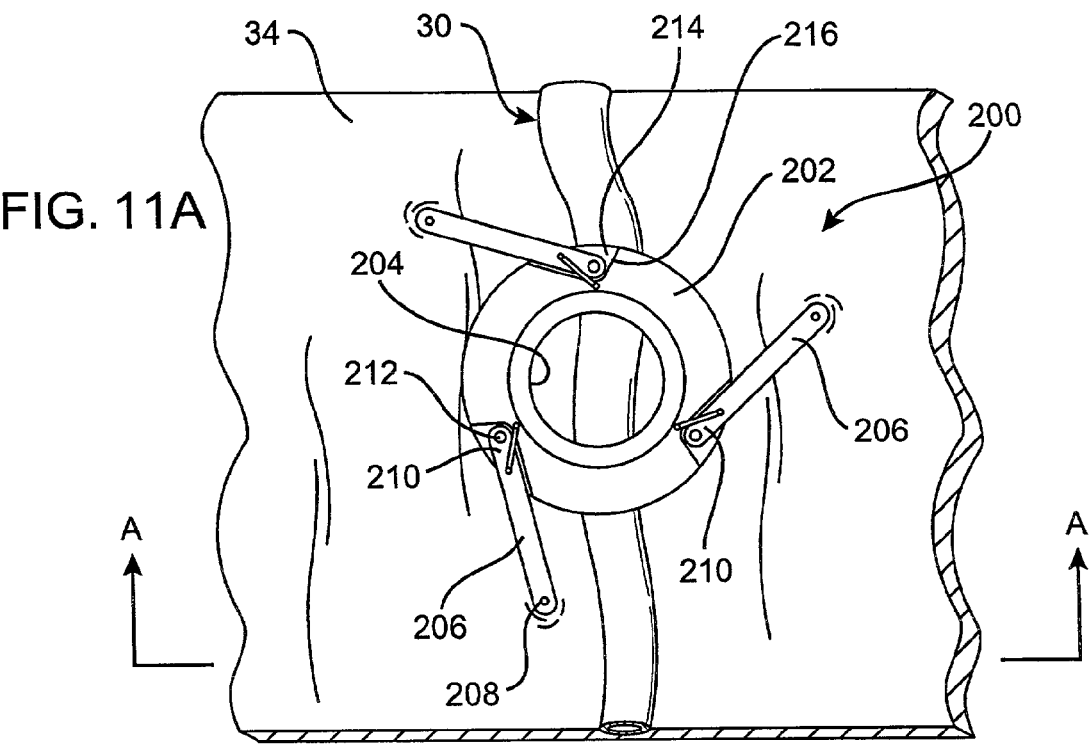
FIGS. 11A–11B are plan views of a tissue engaging device constructed according to another embodiment of the invention, wherein the device is shown engaging the wall of the heart shown in FIGS. 2–2A in non-retracting and retracting orientations, respectively.
Figure 11B:
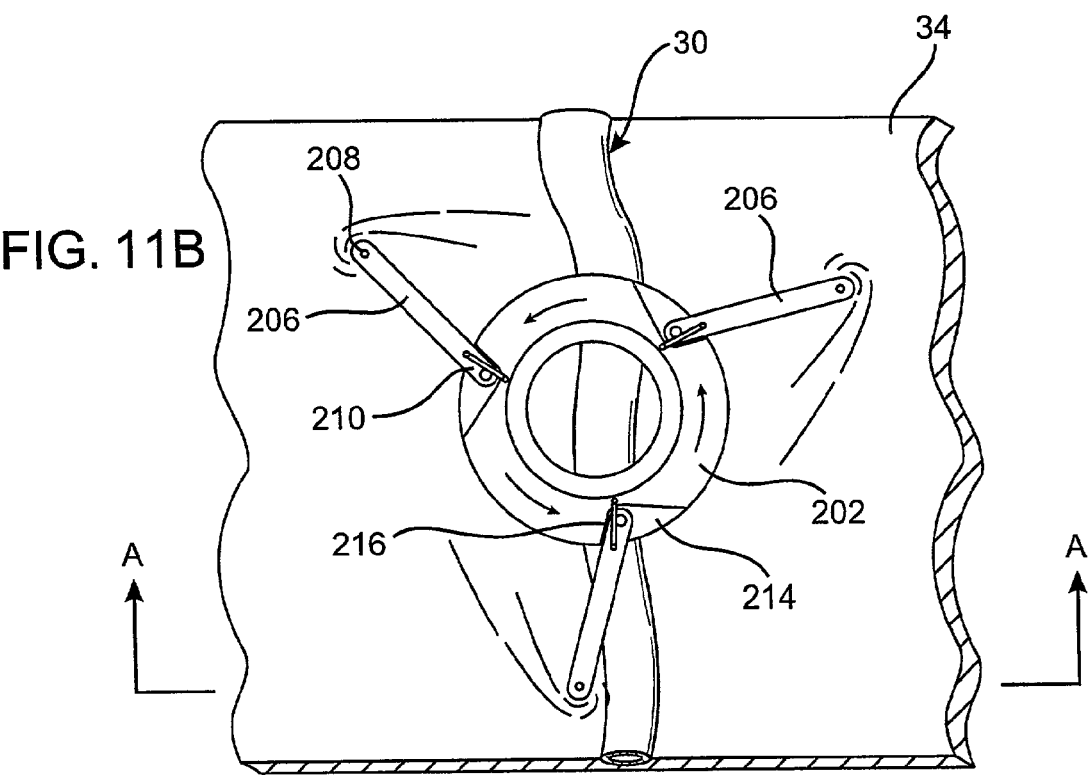

The base 202 has a plurality of recesses 214 each of which mounts an end 210 of a tissue engaging element 206. Each of the recesses 214 has a cam surface 216 that engages the end 210 of a tissue engaging element 206 upon actuating the device in order to retract the cardiac tissue and stabilize the heart. To that end, the device 200 has an actuator to drive the tissue engaging elements 206 and retract tissue. The actuator may comprise rotating the base 202 so as to drive the cam surfaces 216 of recesses 214 against the ends 210 of the tissue engaging elements 206. FIG. 11A shows the device 200 before actuation; FIG. 11B shows the device after the base 202 has been rotated. Each tissue engaging element 206 is preferably biased to the position of FIGS. 11A and 12A by suitable means, such as tension springs extending between the base 202 and the tissue engaging elements 206. The components of the device 200 may be made from any suitable materials; for example, the base may comprise a polymer while the elements 206 are metal.

Figure 12A:
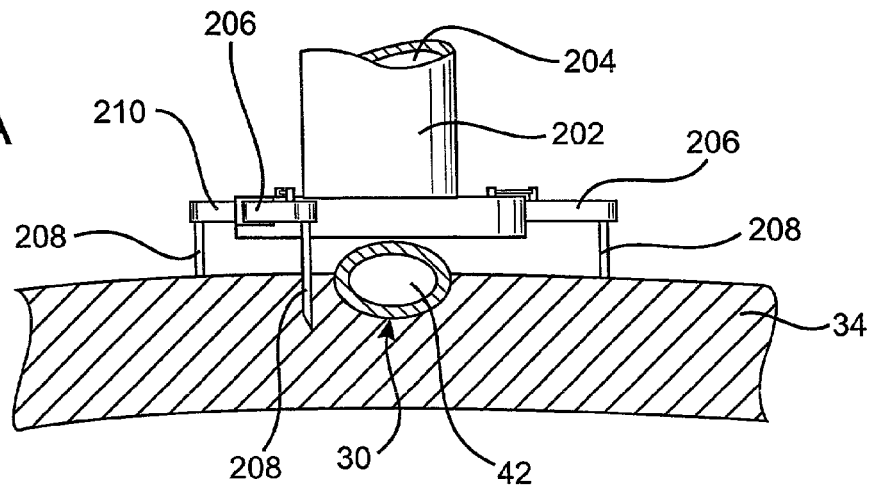
FIGS. 12A–12B are elevation views, in section, taken along lines A—A in FIGS. 11A–11B.
Figure 12B:
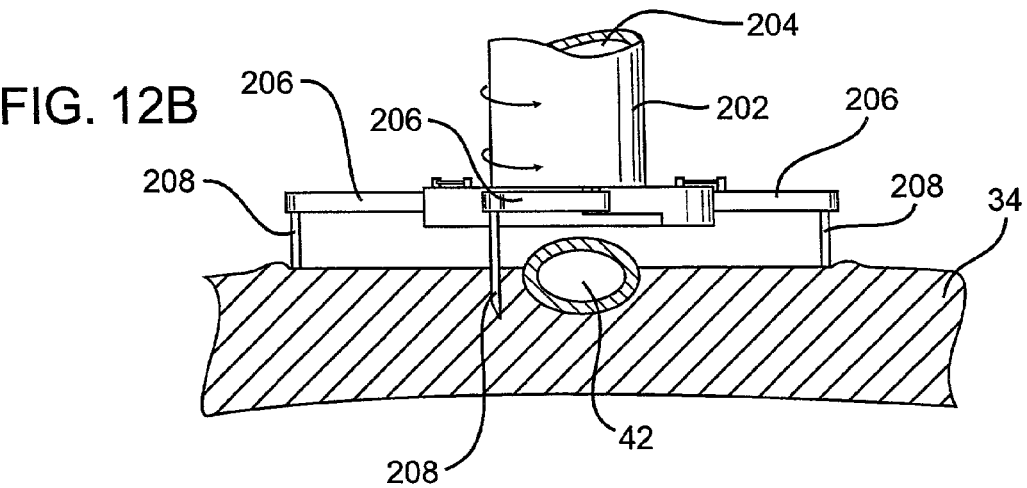

FIGS. 11A–11B and 12A–12B show one possible application for the device 200, retracting the wall of a heart adjacent a coronary vessel to stabilize vessel. The device 200 is positioned on the heart wall 34 so that the opening 204 overlies the LAD 30. The ends 208 of the tissue engaging elements 206 are engaged with the tissue of the heart wall 34 by any suitable means. As shown in FIGS. 12A–12B, the ends 208 may simply have sharp tips which are passed into the tissue to engage the elements with the heart wall.

Figure 13:
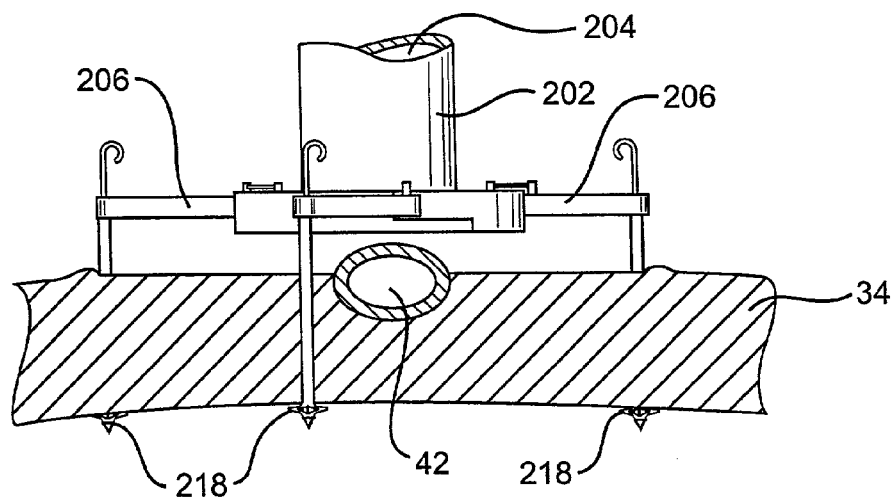
FIG. 13 is an elevation view, in section, of an alternative tissue engaging device constructed according to the embodiment shown in FIGS. 12A–12B.

Alternatively, as shown in FIG. 13, the ends 208 of the tissue engaging elements 206 may have a mechanism for more securely engaging the tissue, such as expandable members 218. The expandable members 218 may be constructed as described above with respect to the embodiment of FIGS. 3A–3B, thereby allowing the ends 208 to be collapsed for passage through the heart wall and then expanded once through the wall in order to positively secure the device 200 to the tissue. The members 218 may be expanded by moving one shaft relative to another as described above.

Once the ends of the tissue engaging elements have been secured to the tissue, as shown in FIGS. 11A and 12A, the base 202 is rotated as described above, which drives the tissue engaging elements relative to the base and the tissue. This action tensions the tissue of the heart wall 34 to retract the wall and stabilize the heart in the area of the coronary vessel, as shown in FIGS. 11B and 12B. As a result, the coronary vessel, which is the LAD 30 in the Figures, is stabilized so that subsequent procedures may be carried out on a relatively stable site. As an example, the device 200 may be used to stabilize the heart while passing a conduit delivery device through the vessel and the heart wall in order to place the vessel in communication with a heart chamber.

According to another embodiment of the invention, a conduit is provided for placing a coronary vessel of a patient's heart in communication with a heart chamber. The conduit comprises a tubular element including first and second portions having different cross-sectional sizes, and a bore defining a blood flow path. The cross-section of the first portion of the tubular element is larger than the cross-section of the second portion of the tubular element. In one preferred embodiment the different cross-sectional configurations are selected to produce a tubular element that is generally funnel-shaped.

According to one aspect of this embodiment, the first and second portions of the tubular element are generally aligned and the bore defines a generally straight blood flow path. According to another aspect of this embodiment, the tubular element is an expandable stent including a bore defining a blood flow path and first and second portions, the first and second portions having different cross-sectional sizes when the stent is expanded. The first and second portions of the stent are preferably constructed to provide the stent with maximum radial strength when expanded.

Figure 14A:
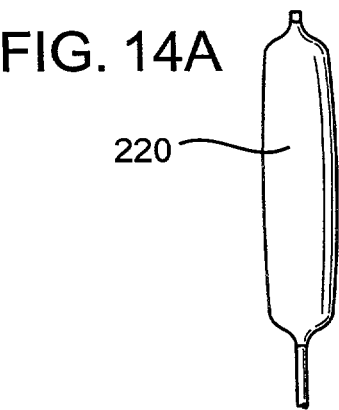
FIGS. 14A–14B are elevation views of a tapered balloon forming part of another embodiment of the invention, wherein the balloon is shown in its collapsed and expanded orientations, respectively.
Figure 14B:
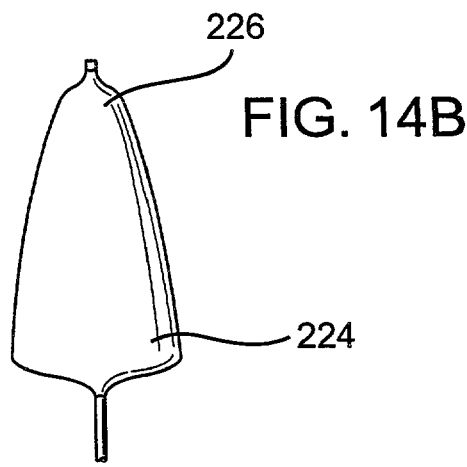
Figure 15A:
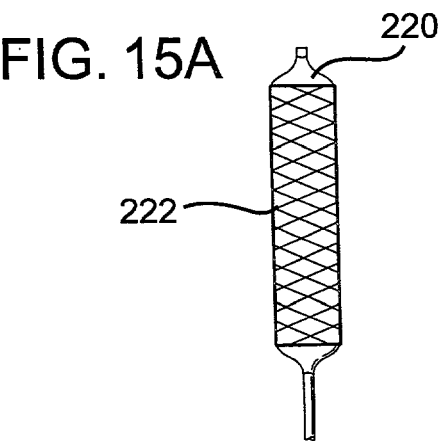
FIGS. 15A–15B are elevation views of an expandable conduit mounted on the tapered balloon shown in FIGS. 14A–14B, the conduit being shown in its collapsed and expanded orientations, respectively.
Figure 15B:
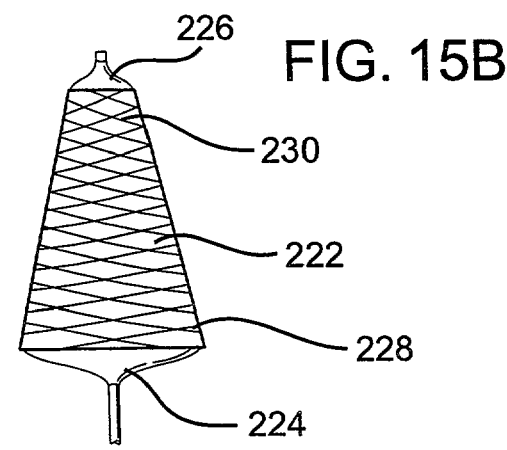

FIGS. 14A–14B and 15A–15B show one preferred system for placing a funnel-shaped conduit in a patient's heart wall to communicate a coronary vessel with a heart chamber. The system includes a balloon 220 and a conduit 222. The balloon 220 is generally straight over its length when unexpanded (FIG. 14A); however, when expanded the balloon 220 assumes a tapered orientation with a large end 224 and a small end 226 (FIG. 14B). The conduit 222 is also preferably straight over its length when supported by the balloon 220 in a collapsed orientation (FIG. 15A) and funnel shaped when expanded by the balloon (FIG. 15B). It should be understood that a tapered balloon is not necessary to expand a tapered or funnel-shaped stent. For example, a straight balloon could be used to expand a stent constructed to assume a funnel-shaped configuration, with the inflated size of the balloon preferably being sufficient to fully expand the large end of the stent.

Figure 16:
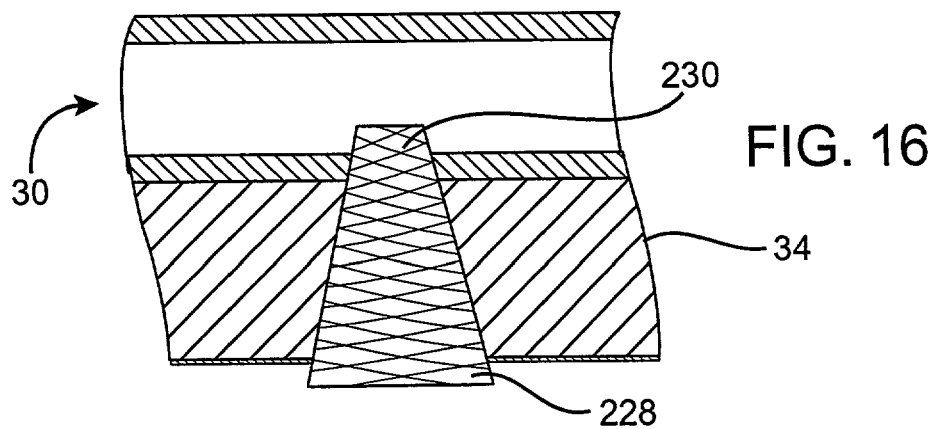
FIG. 16 is an elevation view, in section, of a portion of a heart wall and coronary vessel in which the conduit shown in FIG. 15A–15B has been positioned.

FIG. 16 depicts an exemplary application of the conduit 222 show in FIGS. 15A–15B. The conduit 222 is shown positioned in a heart wall 34 with a large diameter end 228 located in a heart chamber such as the left ventricle 12 and a small diameter end 230 located in a coronary vessel such as LAD 30. It will be appreciated that the shape, size and orientation of the conduit 222 in the heart wall and coronary vessel may be varied from that shown in FIG. 16. For example, the taper of the conduit wall may be non-continuous or more gradual or severe than that shown in the Figures, or either end of the conduit may be flush or within the heart wall. Also, the conduit may be a rigid or expandable tubular element.

FIGS. 17A–17B show one preferred funnel-shaped stent 240 that includes a plurality of stent elements in the form of struts 242 that move relative to each other as the stent moves to its expanded orientation. The struts 242 are joined at nodes 244 which move along with the struts as the stent 240 moves to its expanded orientation. A plurality of open areas are defined between the struts 242 through which blood may flow.

FIG. 17A shows the stent 240 in its collapsed orientation. As shown, the stent 240 comprises a first portion 246, a second portion 248 and a third portion 250. These three portions 246, 248, 250 are designed so that upon expansion they have different diameters or cross-sectional dimensions. This may be achieved by using different length struts 242 for the respective portions 246, 248, 250. The relative dimensions of the struts (and thus the relative size of the expanded portions formed by the struts) may be varied to achieve different sizes and shapes. Referring to FIG. 17B, the illustrated stent 240 is constructed so that the first portion 246 expands to the smallest diameter while the third portion 250 expands to the largest diameter. The second portion 248 expands to a middle diameter that tapers between the portions 246, 250. The struts 242 of the stent 240 preferably assume a maximum load supporting position when fully expanded.

The stent 240 may be used in various applications, including forming a blood flow path between a coronary vessel and a heart chamber. The stent 240 (or another conduit constructed according to this embodiment of the invention) may be used as a coronary stent to improve blood flow through a coronary artery. In this application, the stent 240 would be introduced into a peripheral vessel and guided to the desired artery by conventional means.

Figure 18:
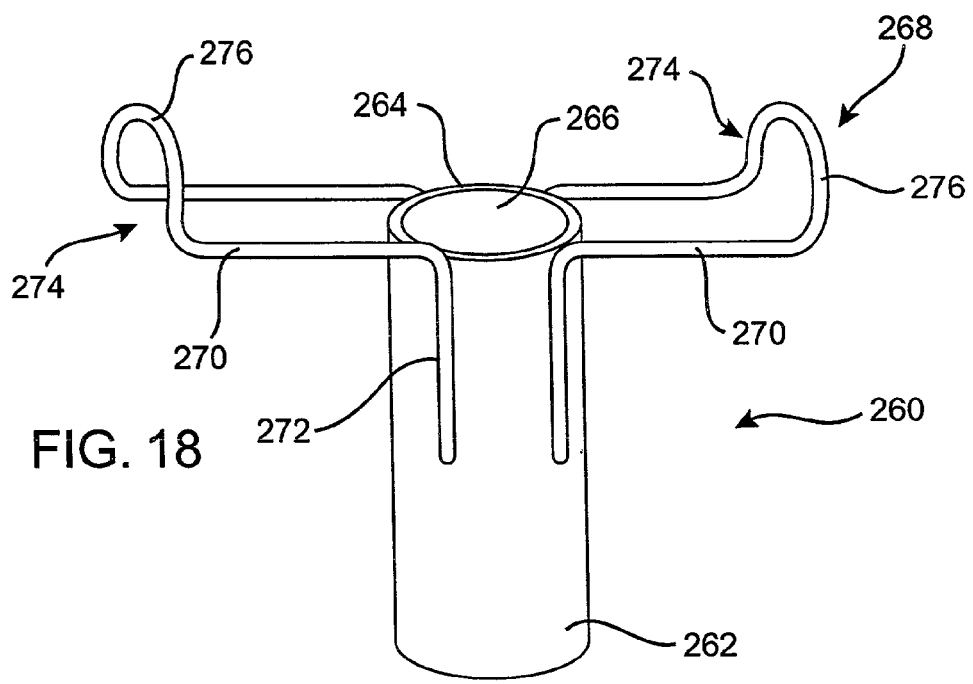
FIG. 18 is a perspective view of another embodiment of the invention providing a conduit for placing a coronary vessel in communication with a heart chamber while internally supporting the interior of the vessel.

FIGS. 18 and 19A–19C show another embodiment of the invention providing a conduit for placing a coronary vessel in communication with a heart chamber, the conduit including a mechanism for internally supporting the interior of the vessel. FIG. 18 shows a conduit 260 in the form of a rigid, tubular element having a first end 262 and a second end 264. The conduit 260 has a bore 266 passing therethrough that defines a blood flow path. A mechanism 268 is provided to support the wall of a coronary vessel with which the conduit 260 communicates. The mechanism 268 includes a pair of support arms 270 preferably in the form of flexible members made from any suitable material, such as stainless steel, nitinol, polymers, etc. A pair of support arms 270 is shown; however, any desired number of arms may be used. Each support arm 270 is secured to the conduit 260 at 272, for example, by welding, brazing or adhesive. Alternatively, the support arms 270 may be integrally formed as part of the conduit 260. The support arms 270 are provided with vessel supporting portions 274 which may be formed by rounded lengths of wire 276, as shown.

Figure 19A:
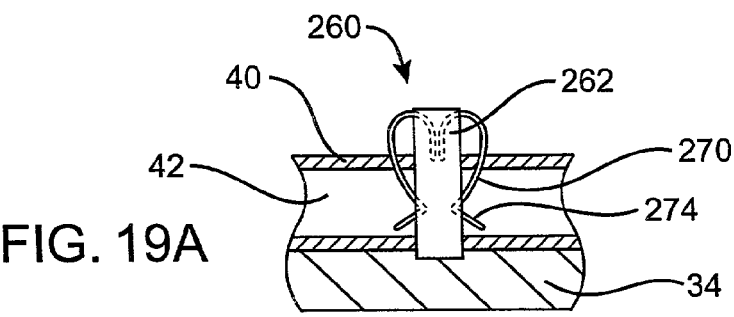
FIGS. 19A–19C are schematic representations of a preferred application for the conduit shown in FIG. 18.
Figure 19B:
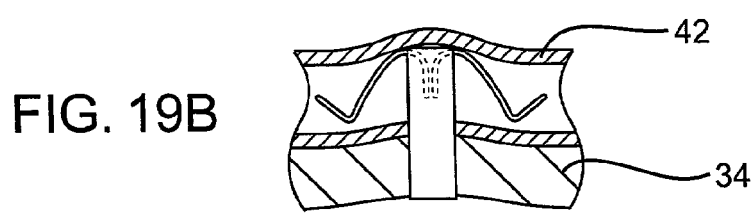
Figure 19C:
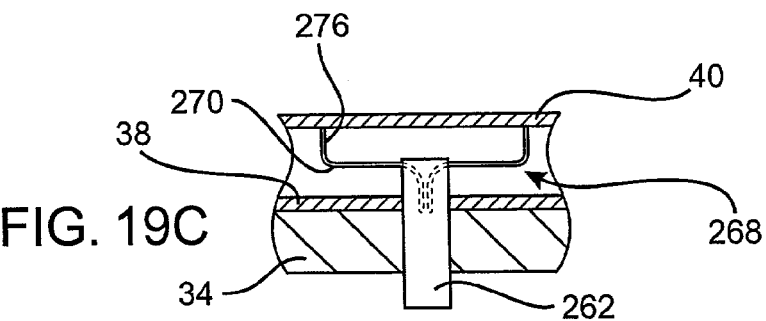

Referring to FIG. 19A, which schematically illustrates one preferred application of the conduit 260, the support arms 270 may be folded against the wall of the conduit 260 so that the conduit assumes a relatively low profile position. The conduit 260 is then passed through an opening in the wall of a coronary vessel such as the LAD 30 (FIG. 19A). The support arms 270 may be constrained against the conduit 260 manually, with an instrument, or with a removable sheath or cover. The conduit 260 is delivered into the lumen 42 of the LAD and the heart wall 34 an amount sufficient to place all (or substantially all) of the support arms 270 inside the outer wall 40 of LAD 30 (FIG. 19B). At this point the support arms 270 spring out to the position shown in FIG. 18, which results in the vessel supporting portions 274 of the arms contacting the walls of the LAD 30 (FIG. 19C). The conduit is preferably configured so that when the support arms are in this position the conduit end 262 extends into the left ventricle 12 while the conduit end 264 extends into the LAD 30.

FIG. 20 shows an another embodiment of a conduit with a vessel supporting mechanism. The conduit is designated 280 and preferably is a rigid tubular element as in the previous embodiment. The conduit 280 has a mechanism 282 that supports the wall of a coronary vessel in which the conduit is placed. The support mechanism 282 includes three support arms 284 in the form of hoops made from any suitable material, as discussed above. The support arms 284 are also preferably flexible and secured to the conduit 280 by welding, brazing or adhesive. The support arms 284 have vessel supporting portions 286 that contact and may slightly distend the vessel wall. While three arms 284 are shown, any desired number may of course be used.

FIG. 21 shows still another embodiment of a conduit with a vessel supporting mechanism. The conduit is designated 290 and preferably is a rigid tubular element as in the previous embodiments. The conduit 290 is provided with a mechanism 292 for supporting the wall of a coronary vessel. The vessel support mechanism 292 includes a first pair of support arms 294 and a second pair of support arms 296 in the form of tabs made from any suitable material, as discussed above. The support arms 294 extend generally along the longitudinal axis of the conduit 290 and are adapted to contact the outer wall of a coronary vessel, while the support arms 296 extend radially from the conduit 290 and are adapted to contact the inner wall of the vessel. The support arms 294, 296 are preferably integrally formed with the conduit 290 and are flexible to assume a low profile position. It will be noted that the support arms 294, 296 could be separate members secured to the conduit by suitable means such as welding, brazing or adhesive. Also, although three arms 284 are shown, any desired number may be used.

FIG. 22 shows yet another embodiment of a conduit with a vessel supporting mechanism. The conduit is designated 300 and, instead of being a rigid tubular element as in the previous embodiments, is an expandable tubular element, for example, a coronary stent. The conduit 300 has stent elements in the form of struts 302 joined at nodes 304. The conduit 300 may be formed substantially in the same manner as the stent 240 in FIGS. 17A–17B. The conduit 300, however, is provided with a mechanism 306 for supporting the wall of a coronary vessel. The vessel support mechanism 306 in this embodiment includes a pair of extensions 308 that are preferably formed as an integral part of the stent struts 302. The extensions 308 extend generally along the longitudinal axis of the conduit 290 so as to contact the outer wall of a coronary vessel, thereby supporting the wall in the manner discussed above. The ends 310 of the extensions 308 may be unattached, as shown, or attached.

The conduit 300 may be mounted on a balloon or other expandable member (not shown) in a collapsed orientation for introduction into the coronary vessel and the heart wall. The extensions 308 can be loaded on the balloon with the remaining portion of the conduit 300. Once properly positioned in the heart wall, the balloon is inflated to expand the conduit 300 to the orientation shown in FIG. 22. It should be recognized that this embodiment of the invention may be carried out using any expandable conduit, the particular stent shown in FIG. 22 representing only one possible construction. Also, the extensions 308 could be separate members secured to the conduit 300 by suitable means such as welding, brazing or adhesive. Finally, although two extensions 308 are provided on the illustrated conduit, any number of extensions may be used.

It should be noted that, as used herein, the term conduit refers to any structure that is capable of conveying fluid from one point to another, for example, a tubular element with two or more open ends. In view of the fact that various characteristics of the conduit, for example, size, shape and surface configuration, may vary depending on the application, it will be recognized that the conduits in the illustrated embodiments are merely exemplary. For instance, the conduit could be a rigid, flexible or expandable tubular element formed of metal, polymers or composite materials having solid or perforated walls. The conduit could be straight over its length with the ends aligned or the ends could be offset, the exterior surface of the conduit may be treated to enhance fixation of the conduit in the heart wall, and the conduit may or may not include a valve or other flow controlling mechanism. Further, a conduit constructed according to the invention may be used to deliver various pharmaceutical substances, such as angiogenic growth factors or other substances that aid in the perfusion of surrounding myocardial tissue.

It will be understood that the LAD 30 illustrated in the Figures is but one example of a possible vessel which may be placed in communication with a heart chamber.

Similarly, in the preferred embodiments the LAD 30 is placed in communication with a heart chamber that contains blood, which, in the illustrated embodiments, is the left ventricle 12. It will be understood, however, that the invention may be used to place a conduit in communication with any source of blood (arterial or venous), for example, another heart chamber such as the left atrium, or the aorta, pulmonary veins, etc.

It also will be appreciated that the various devices of the invention incorporated in the illustrated embodiments may be used together or separately, and the methods may be modified, carried out by combining particular steps, or varying the sequence of steps. Further, it will be understood that the embodiments may be used in various types of procedures, for example, the surgical approach depicted in FIG. 1, an open surgical procedure including a median sternotomy, or a minimally invasive procedure utilizing one or more relatively small access openings or ports. Endoscopes or thoracoscopes may be used for visualization if the procedure is truly minimally invasive. Additionally, rather than forming one or more incisions in the patient's chest wall, an endovascular approach may be used to guide various inventive devices to the heart through the patient's vascular system to the heart, for example, by introducing the devices into a peripheral vessel such as the femoral artery. Similarly, the different embodiments may be used in beating heart procedures, stopped-heart procedures utilizing cardiopulmonary bypass (CPB), or procedures during which the heart is intermittently stopped and started.

The preferred embodiments of the invention are described above in detail for the purpose of setting forth a complete disclosure and for sake of explanation and clarity. It will be readily understood that the scope of the invention defined by the appended claims will encompass numerous changes and modifications.

What is claimed is:

1. A method for placing a generally funnel-shaped conduit in a wall of a patient's heart to communicate a heart chamber with an interior of a coronary vessel located near the exterior of the heart, the method comprising steps of: (a) providing a conduit having a length, a first end, and a second end, wherein the conduit is generally straight and the second end has a larger cross-section than the first end, as measured at exterior and interior surfaces thereof, such that the conduit is generally funnel-shaped; (b) positioning the conduit in the wall of the heart to communicate the heart chamber with the interior of the coronary vessel; and (c) orienting the conduit in the wall of the heart such that the first end is disposed adjacent the coronary vessel and the second end is disposed adjacent the heart chamber.

* * * * *